(12) United States Patent
Ralph

(10) Patent No.: US 11,166,625 B2
(45) Date of Patent: Nov. 9, 2021

(54) SHEATH WITH DETECTABLE LEADER

(71) Applicant: Spiration, Inc., Redmond, WA (US)

(72) Inventor: Christopher R. Ralph, Woodinville, WA (US)

(73) Assignee: Spiration, Inc., Redmond, WA (US)

( * ) Notice: Subject to any disclaimer, the term of this patent is extended or adjusted under 35 U.S.C. 154(b) by 87 days.

(21) Appl. No.: 15/936,092

(22) Filed: Mar. 26, 2018

(65) Prior Publication Data
US 2019/0290107 A1 Sep. 26, 2019

(51) Int. Cl.
*A61B 1/012* (2006.01)
*A61B 1/00* (2006.01)
*A61B 5/06* (2006.01)
*A61M 25/06* (2006.01)

(52) U.S. Cl.
CPC .......... *A61B 1/00135* (2013.01); *A61B 5/064* (2013.01); *A61M 2025/0687* (2013.01); *A61M 2205/0216* (2013.01)

(58) Field of Classification Search
CPC .............. A61B 1/0008; A61B 1/00098; A61B 1/00101; A61B 1/00135; A61B 1/00154; A61B 1/012; A61B 1/018
See application file for complete search history.

(56) References Cited

U.S. PATENT DOCUMENTS

| | | | | |
|---|---|---|---|---|
| 5,499,630 A | * | 3/1996 | Hiki | A61B 1/0051 600/104 |
| 6,224,555 B1 | * | 5/2001 | Ouchi | A61B 1/018 600/439 |
| 8,727,988 B2 | * | 5/2014 | Flaherty | A61B 8/12 600/439 |
| 9,820,724 B2 | * | 11/2017 | Mamiya | A61B 1/06 |
| 2006/0189972 A1 | * | 8/2006 | Grossman | A61B 18/1477 606/32 |
| 2007/0038089 A1 | * | 2/2007 | Hatano | A61B 8/12 600/437 |
| 2007/0249939 A1 | * | 10/2007 | Gerbi | A61B 8/0841 600/462 |
| 2012/0078094 A1 | * | 3/2012 | Nishina | A61B 1/00098 600/431 |
| 2014/0025004 A1 | | 1/2014 | Falk et al. | |
| 2016/0367233 A1 | * | 12/2016 | Mamiya | A61B 1/00 |
| 2017/0007103 A1 | * | 1/2017 | Hashiguchi | A61B 1/0125 |

* cited by examiner

*Primary Examiner* — Allen Porter
(74) *Attorney, Agent, or Firm* — Clements Bernard Baratta; Frank J. Bozzo

(57) ABSTRACT

Disclosed embodiments include apparatuses, systems, and methods for providing a sheath tip with an angled distal face to conform the sheath to a surface of tissue toward which the sheath is being extended to potentially help reduce or avoid tissue damage upon extending a sheath to convey an elongated instrument for sampling or treatment. In an illustrative embodiment, an apparatus includes a sheath tip positionable at an end of a sheath configured to convey an elongated medical instrument to a location adjacent a detection range of a detecting device. The sheath tip includes a distal member that extends a finite distance beyond the end of the sheath. The distal member is detectable by the detecting device when the end of the sheath is within the finite distance of the detection range of the detecting device.

20 Claims, 7 Drawing Sheets

SHEATH WITH DETECTABLE LEADER

FIELD

The present disclosure relates to a sheath used to extend an elongated instrument.

BACKGROUND

The statements in this section merely provide background information related to the present disclosure and may not constitute prior art.

The ability to access tissue within a patient's body without invasive surgery allows for ever-improving types of analysis, diagnosis, and treatment with reduced pain, reduced recovery time, and a reduced risk of complications. By way of two examples, endoscopic and catherization techniques have enabled evaluation and treatment of numerous internal lesions without invasive surgery.

For example, suspected or actual lesions may be sampled or treated by extending an elongated medical instrument, such as a sampling needle, through a sheath that is positioned by an insertion control system, such as a bronchoscope or an endoscope. The sheath may be extended from the insertion control system to position the elongated medical instrument, then the elongated instrument itself may be deployed for sampling or treatment.

Use of the insertion control system, while possibly avoiding invasive surgery, may pose its own challenges. For example, because the insertion control system may operate in tight spaces, it may be a challenge to engage in sampling or treatment at a desired position within in a body while minimizing or attempting to avoid or minimize trauma to the tissue at or near the desired position or other undesirable effects resulting from contact between the insertion control system and tissue walls. Although the insertion control system may include one or more sensing apparatuses to detect tissue of interest and/or to monitor a location of the elongated medical instrument used in a procedure, it nonetheless may present a challenge to verify a position of the elongated instrument without potentially causing trauma to tissue within the body or other undesirable effects.

SUMMARY

Disclosed embodiments include apparatuses, systems, and methods for providing a sheath tip with a distal member that may enable detection or verification of a position of a distal end of a sheath without extending the sheath to a position that potentially could impact or traumatize tissue or result in other undesirable effects from the distal end of the sheath pushing against tissue.

In an illustrative embodiment, an apparatus includes a sheath tip positionable at an end of a sheath configured to convey an elongated medical instrument to a location adjacent a detection range of a detecting device. The sheath tip includes a distal member that extends a finite distance beyond the end of the sheath. The distal member is detectable by the detecting device when the end of the sheath is within the finite distance of the detection range of the detecting device.

In another illustrative embodiment, a system includes a sheath defining therein a lumen and that is configured to be extendable toward a tissue at an angle to a surface of the tissue. An elongated medical instrument is configured to be delivered through the lumen in the sheath. An insertion control system is configured to convey the sheath along an axis to a desired location. The insertion control system includes a detecting device disposed one of at and adjacent to an end of the insertion control system and has a detection range. The insertion control system also has a first side from which the sheath is configured to be extended along an axis toward a surface. An instrument control system is configured to direct operation of the elongated medial instrument when the elongated medical instrument reaches a desired position. A sheath tip is positionable at an end of a sheath configured to convey an elongated medical instrument to a location adjacent the detection range of a detecting device. The sheath tip includes a distal member that extends a finite distance beyond the end of the sheath. The distal member is detectable by the detecting device when the end of the sheath is within the finite distance of the detection range of the detecting device.

In a further illustrative embodiment, a method includes preparing an elongated instrument for being conveyed into a body through a lumen in a sheath, where the sheath is to be extended toward a desired location adjacent a detection range of the detecting device. The sheath includes a sheath tip at an end of the sheath, where a distal end of the sheath tip includes a distal member that extends a finite distance beyond the end of the sheath so that the distal member is detectable by the detecting device when the end of the sheath is within the detection range of the detecting device. The sheath conveying the elongated instrument into the body is inserted into the body.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

The following description is merely illustrative in nature and is not intended to limit the present disclosure, application, or uses. It will be noted that the first digit of three-digit reference numbers correspond to the number of the figure in which the element first appears.

The following description explains, by way of illustration only and not of limitation, various embodiments of sheath tips having a distal member to aid in verifying a position of a sheath and an elongated instrument that is housed therein. As will be described in detail below, various illustrative embodiments of a sheath tip with a distal member are configured so that the distal member will extend into a detection range of a detecting device before an end of the sheath reaches the detection range, thereby enabling a position of the sheath to be verified without extending the sheath to a point where the sheath potentially may undesirably impact adjacent tissue.

Figure 1:
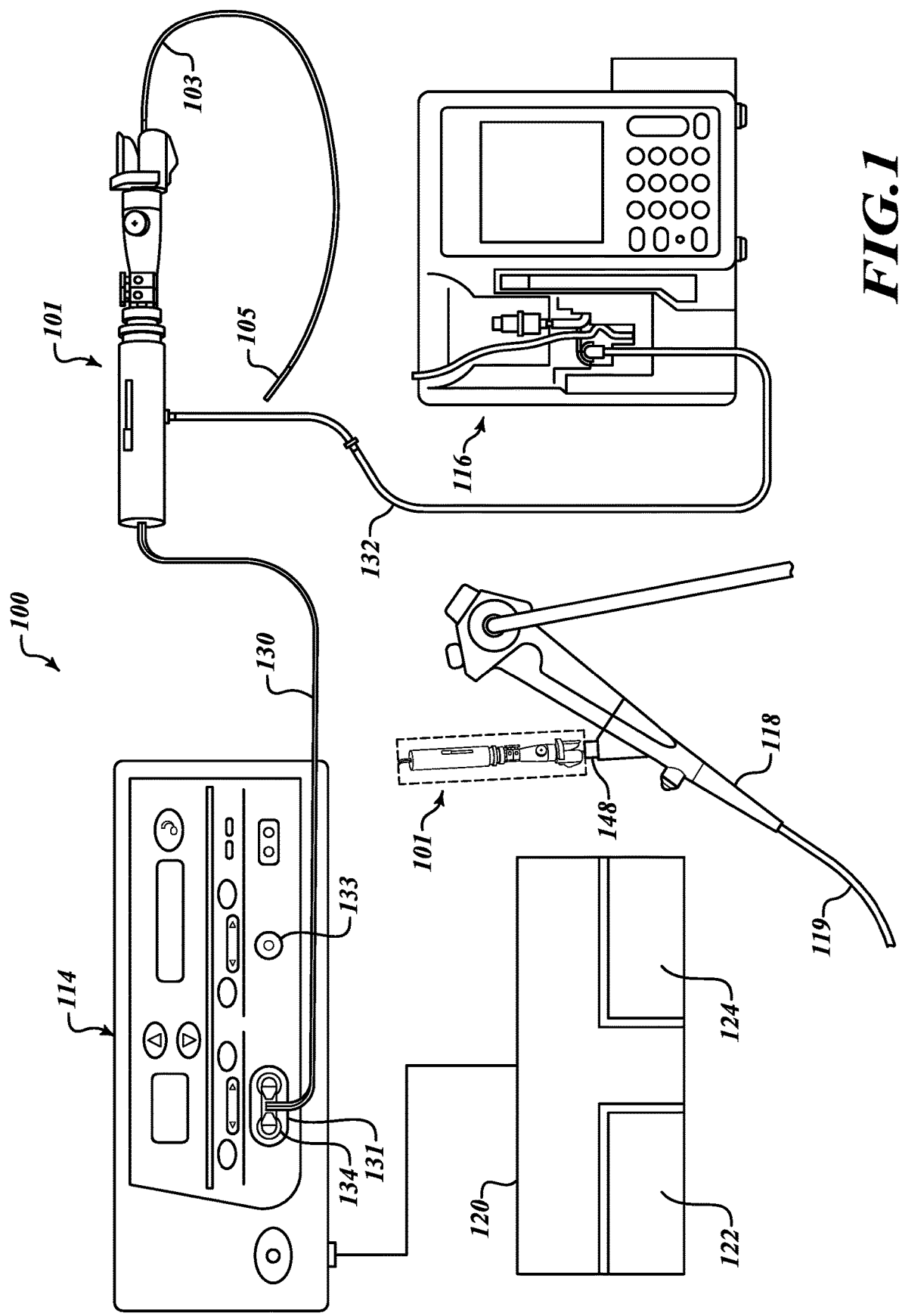
FIG. 1 is a block diagram in partial schematic form of an illustrative system for sampling or treating tissue.

Referring to FIG. 1, in various embodiments, an illustrative system 100 is provided for sampling or treating tissue at a reference point in an anatomical region of a patient (not shown in FIG. 1). For one example, the system 100 may include a sampling device with a vacuum system for drawing a sample via a sampling needle. Alternatively, the system 100 may be a bipolar radio frequency (RF) system, as desired, for using electrical current to ablate or coagulate tissue in a patient. Further alternatively, the system 100 may include a mechanical or laser-based cutting system for incising tissue in a patient. Any such system may involve insertion of an elongated instrument into a patient to perform a desired procedure, and any such elongated instrument may be inserted into a patient via a sheath which may desirably end in a sheath tip as disclosed herein.

In some embodiments, the system 100 includes an elongated medical instrument controllable by a user interface 101, one or more instrument control systems 114 and 116, an insertion control system 118, and various supporting apparatuses. The user interface 101 may include a positioning device for positioning a distal end 113 of a sheath 103 relative to a position of interest in a body (not shown). The user interface 101 also may be configured to direct a position of an elongated instrument (not shown) that is housed within the sheath 103. The elongated instrument, for example, may include a sampling needle, as described below with reference to FIGS. 3, 6, and 7, one or more electrodes, an imaging device, a probe, a cutting device, or any other elongated device. The one or more control systems 114 and 116 may be coupled to the elongated instrument and include devices to draw fluid or tissue, provide electrical current, provide fluid, monitor sensor data, or to perform other functions.

The insertion control system 118 may include a bronchoscope, an endoscope, or another insertion system configured to maneuver an insertion device 119 that may be equipped with a steering mechanism as well as optical, ultrasound, or other sensors to monitor the course of the insertion device 119. The user interface 101 may be received into the insertion control system 118 so that the insertion control system 118 at a port 148 for the insertion control system 118 so that the insertion control system 118 may direct the insertion device 119 to convey the distal end 113 of the sheath 103 to a desired location in a body where the user interface 101 then may be used to manipulate an associated elongated instrument to perform a desired function.

The system may represent any number of sampling or treatment systems. For one example, the system 100 may be a sampling system to collect a tissue sample using a sampling needle, such as described further below with reference to FIGS. 3, 6, and 7. In such case, the insertion control system 118 may include a bronchoscope if the sample is to be collected from a respiratory system or an endoscope if the sample is to be collected from a digestive system. One instrument control system 114 may be used to receive and process sensor data and be operated by controls 120, 122, and 124. Another instrument control system 116 may be a pump or other vacuum source to draw a tissue or fluid sample from the sampling needle that may extend from the distal end 113 of the sheath 103.

For another example, the system 100 may be a cutting system for cutting through a tissue obstruction. In such case, the insertion control system 118 may include an endoscope to direct the if the sample is to be collected from a digestive system. One instrument control system 114 may be used to receive and process sensor data and be operated by controls 120, 122, and 124. Another instrument control system 116 may be a cutting control system to motivate a reciprocating and/or rotating cutting apparatus extending from the distal end 113 of the sheath 103.

For still another example, the system 100 may be an electrosurgical radio frequency (RF) system for ablating, cauterizing, or coagulating tissue. In such case, the insertion control system 118 may include a bronchoscope if the sample is to be collected from a respiratory system or an endoscope if the sample is to be collected from a digestive system. One instrument control system 114 may be a generator operating as a switchable power source 114 to apply electrical power to an elongated instrument extending from the distal end 113 of the sheath. The user interface 101 electrically communicates with the switchable power source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. The switchable power source 114 can be operated with the use of a foot operated unit 120 electrically connected to the switchable power source 114. The foot operated unit 120 may include, for example, a pedal 122 that instructs the switchable power source 114 to apply electrical power to electrode(s) (described below) to cut and/or ablate tissue and a pedal 124 that instructs the generator 114 to apply a lower quantity of electrical power to the electrode(s) to coagulate tissue.

The user interface 101 is further connected to the conductive fluid source 116 with a tube 132 that facilitates the flow of liquid, for example saline solution or another conductive fluid, from the conductive fluid source 116 to the user interface 101. Another instrument control system 116 may be a conductive fluid source 116, such as an infusion pump controllable by a switch, to provide a conductive fluid to the distal end 113 of the sheath 103, where the conductive fluid may be vaporized by applied electrical power to generate heat to ablate or cauterize tissue.

The system 100 may include any number of medical systems or non-medical systems in which an elongated instrument is extended via a sheath 103 to perform an operation, and sheath tips in accordance with the present disclosure may be applied to the distal end 113 of the sheath 103 to facilitate such operations. Embodiments of the sheath tips of the present disclosure are not limited to use with any particular systems or functions. Any applications for use of the sheath tips of the present disclosure are provided solely for illustration and should not be taken as limiting.

Figure 2:
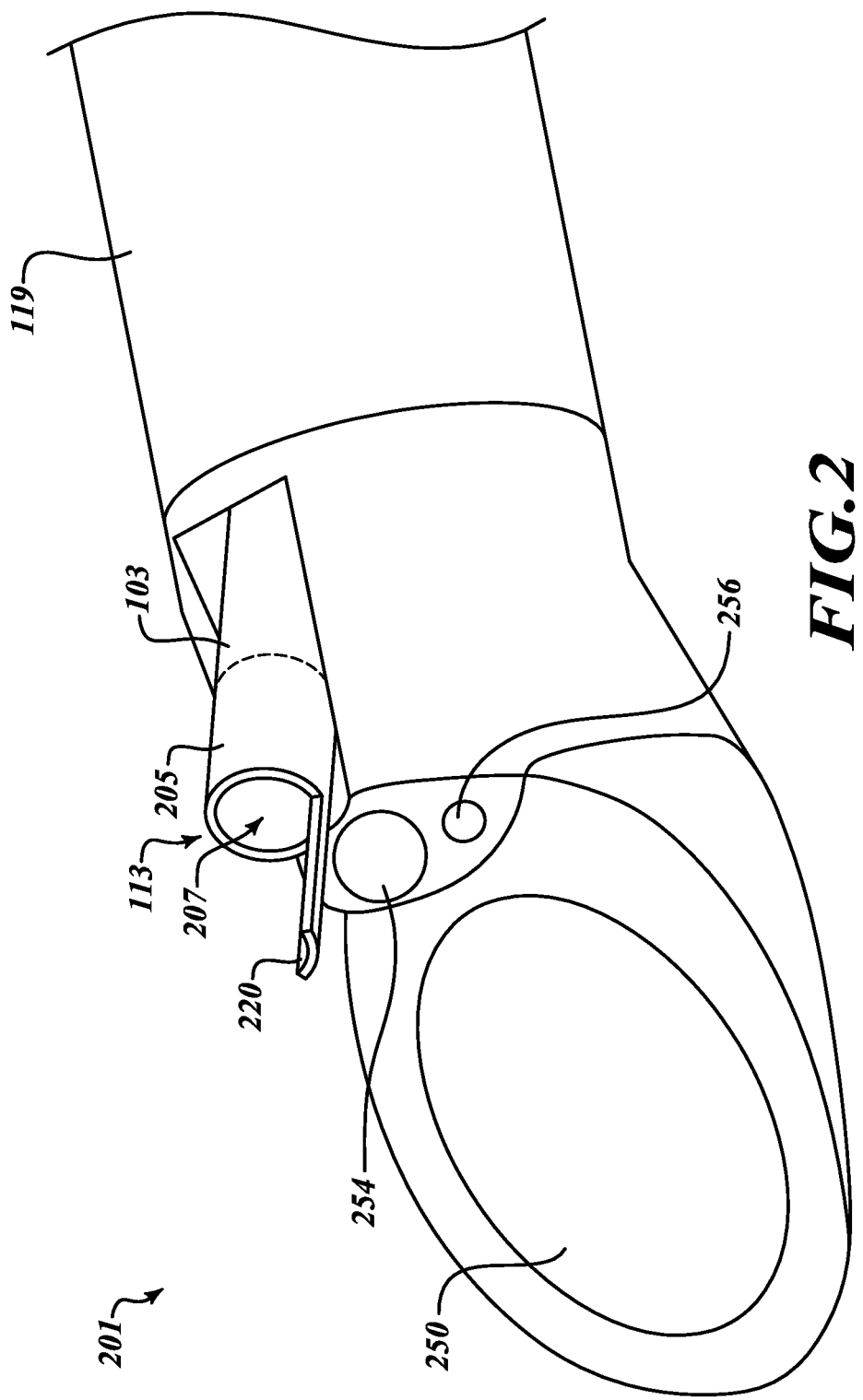
FIG. 2 is a perspective view of a head on an insertion device including a sheath fitted with an illustrative embodiment of a sheath tip with a distal member.

Referring to FIG. 2, a head 201 of the insertion device 119 includes various sensor devices or related devices 250, 254, and 256 usable in positioning the distal end 113 of the sheath 103 (FIG. 1). For example, the head 201 may support an ultrasound transducer 250 that emits ultrasound energy and receives reflected ultrasound energy. The head 201 also may support a camera 254, for which a light source 256 may be provided to illuminate a region adjacent the head 201. The ultrasound transducer 250 and/or the camera 254 may be used to identify lesions or other regions of interest to be sampled or treated by an elongated instrument (not shown in FIG. 2) to be conveyed through the sheath 103.

The distal end 113 of the sheath 103 defines therein a lumen 207 from which the elongated instrument (not shown in FIG. 2) may extend. The distal end 113 of the sheath may be fitted with an embodiment of a sheath tip 205 that includes a distal member 220. The distal member 220 projects beyond the distal end 113 of the sheath 103 toward the sensor devices or related devices 250, 254, and 256, as will be described further below.

Figure 3:
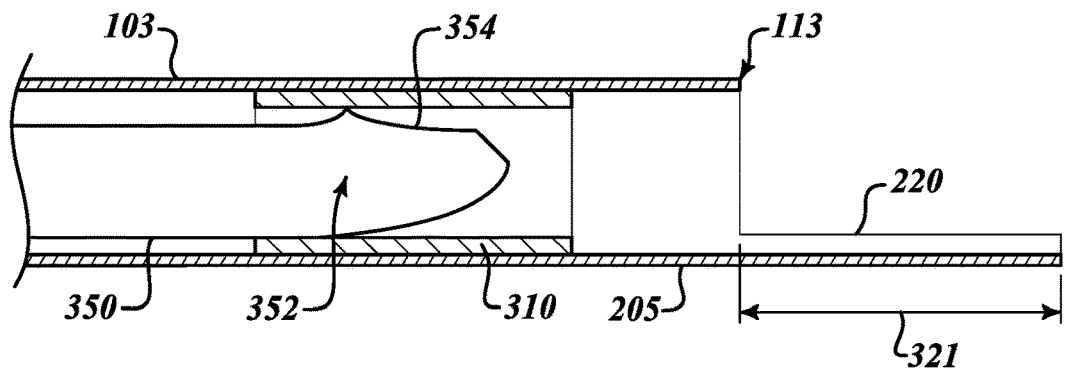
FIG. 3 is a cutaway view of an end of a sheath configured with an illustrative embodiment of a sheath tip having a distal member

Referring to FIG. 3, a sheath 103 houses an elongated instrument 350. The elongated instrument 350 is a sampling needle configured to draw a tissue sample from a tissue surface, lesion, or other body, and it includes an interior lumen 352 that terminates in an open sampling end 354. The elongated instrument 350 may be extended from the sheath 103 to collect a sample of tissue (not shown) at the open sampling end 354 that is then drawn through the lumen 352 by a vacuum source for collection and testing. As described in detail with reference to FIG. 1, however, it should be understood that the elongated instrument 350 may include any of a number of instruments including electrodes, cutting devices, other apparatuses, and the sampling needle is used here only by way of illustration and not limitation.

The sheath tip 205 may be integrally formed with the sheath 203 at the distal end 213 of the sheath 103. The sheath tip 205 may be molded, extruded, or otherwise formed as part of the sheath 103 when the sheath 103 is formed. The distal member 220, which extends a finite distance 312 beyond the distal end 113 of the sheath 103, similarly may be molded, extruded, or otherwise formed as part of the sheath 103 when the sheath 103 is formed. The distal member 220 also may be formed by cutting away a portion of the sheath 103 at the distal end 113 to form the distal member 220. The sheath 103, the sheath tip 205, and the distal member 220 may be formed of plastic or any other flexible material.

In other embodiments, the sheath tip 205 may be a separately formed structure that is then joined to the sheath 103. In such embodiments, the sheath tip 205, including the distal member 220, may be molded, extruded, or otherwise formed separately from the sheath 203. The sheath tip 205 may be formed of plastic or any other suitable flexible material. The sheath tip 205 may be joined to the sheath 103 by adhesives, heat welding, or any other technique that is operable to join together the materials that comprise the sheath 103 and the sheath tip 305.

The sheath 103 may be fitted with an insert 310 that is insertable or otherwise receivable within the sheath 103. The insert may serve the purpose of stiffening the sheath 103 short of the distal end 113 for purposes of assisting extension of the sheath 103 through the insertion device 119 and the head 201 (FIGS. 1 and 2). The insert 310 also may protect the sheath 103 from potential damage that may be caused by the elongated instrument 350, such as might be caused by a potentially sharp open sampling end 354 of a sampling needle while the sheath 103 and/or the insertion device 119 are maneuvered to a desired location within a body (not shown). The insert 110 may be received within the distal end 113 of the sheath 103 just inside the sheath tip 205. If the sheath tip 205 is a separately formed structure joined to the sheath 103, the sheath tip 205 may be situated at an end or beyond an end of the insert 310, or the sheath tip 205 may partially or entirely overlap the insert 310.

Figure 4A:
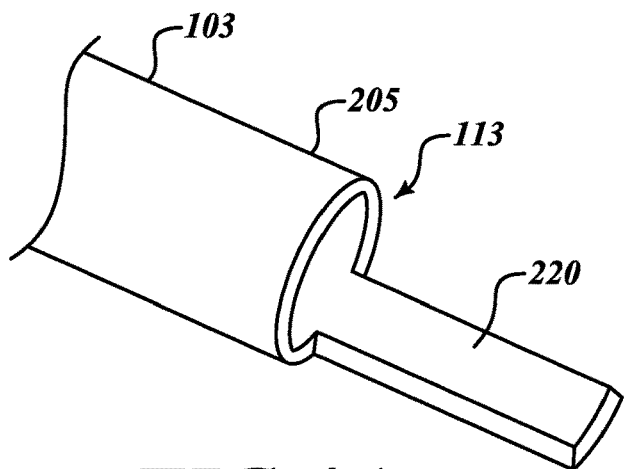
FIGS. 4A and 4B are perspective views of sheath tips including illustrative embodiments of a distal member.
Figure 4B:
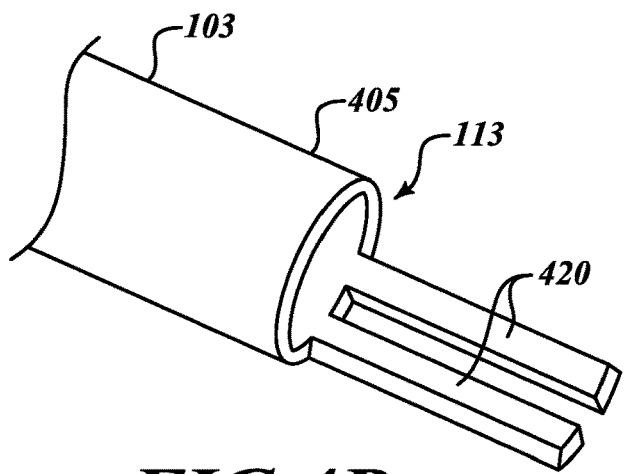

Referring to FIGS. 4A and 4B, sheath tips 205 and 305 having different configurations of distal members 220 and 320, respectively. Referring to FIG. 4A, the sheath tip 205 at the distal end 113 of the sheath 103 includes the single distal member 220, as shown in FIGS. 2 and 3. However, as shown in FIG. 4B, instead of a single distal member 220, the sheath tip 305 at the distal end of the sheath 103 includes multiple distal members 320. Different configurations may have different potential advantages. To name just one example, using a sheath tip such as the sheath tip 405 that includes multiple distal members 420, may allow one of the distal members 420 to extend so as to be detected by a detecting device if another of the distal members 420 is blocked by tissue or another structure.

Figure 5:
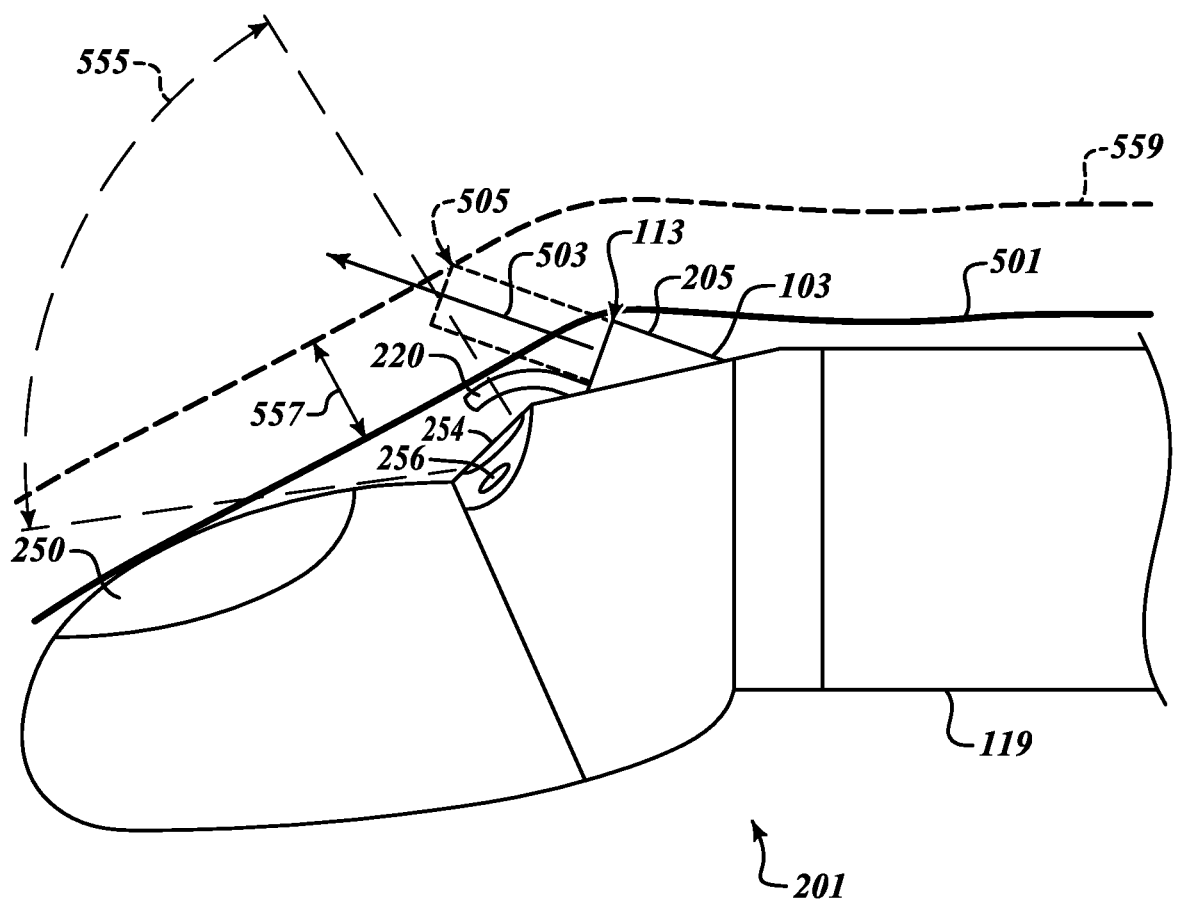
FIG. 5 is a side view of the head of the insertion device of FIG. 2 after extension of the sheath including an illustrative embodiment of a sheath tip having a distal member.

Referring to FIG. 5, the head 201 is disposed adjacent a tissue surface 501, such as an interior surface of a bodily tract into which the head 201 may be inserted. If the sheath 103 were to be extended further, the sheath 103 would extend along an axis 503. A detection range 555 of a detecting device, such as the field of view or visual range of the camera 254, shows an area in which an object may be detected to verify its position.

The distal member 220 of the sheath tip 205 may allow a position of the sheath 103 to be verified while potentially minimizing or avoiding undesirable or undue impact with the tissue surface 501. A projection 505 shows a position to which the sheath 103 may be extended before the distal end 113 of the sheath 103 would be extended if the sheath 103 did not include the sheath tip 205 with the distal member 220. As shown by the projection 505, the sheath 103 may have to be extended well beyond an intersection with the tissue surface 501, potentially impacting and/or distending the tissue surface 501, before the distal end 113 of the sheath 103 extends into the detection range 555. The extension of the sheath 103 shown by the projection 505 thus potentially may result in unwanted contact with the tissue surface 501. Extending the sheath 103 far enough to reach the detection range 555 may have undesirable effects. For one example, the extension of the sheath 103 against the tissue surface 501 may displace the head 201 from the tissue surface 501, moving the tissue surface 501 away a relative distance 557 to a new surface location represented by dotted line 559. (It will be appreciated that the relative displacement of the head 201 from the tissue surface 501 may be as a result of movement of the head 201 away from the tissue surface 501, movement of the tissue surface 501 from the head 201, or some combination of movement of the head 201 and the tissue surface 501.) Such displacement may, therefore, displace the ultrasound transducer 250 from the tissue surface 501 and impair the ability of the ultrasound transducer 250 to scan tissues at or behind the tissue surface 501. For another example, extension of the sheath 103 as shown by the projection 505 may distend or traumatize tissue at the tissue surface 501.

By contrast, by equipping the sheath 103 with a sheath tip 205 with the distal member 220, the distal member 220 already extends into the detection range 555 without further extension of the sheath 103. When the distal member 220 is deformable, the distal member 220 may deflect off the tissue surface 501 and into the detection range 501 with minimal impingement by the distal end 113 of the sheath 103 upon the tissue surface. By being able to identify a position of the sheath tip 205 and, thus, a position of the sheath 103, potential damage to the head 201 or other devices may be avoided. For example, being able to verify that the sheath tip 205 has been extended from the head 201 as desired may avoid damage to either tissue or to a channel within the head 201 by attempting extend a needle or other elongated instrument from the sheath 103 before the sheath 103 is desirably extended from the head 201.

Figure 6:
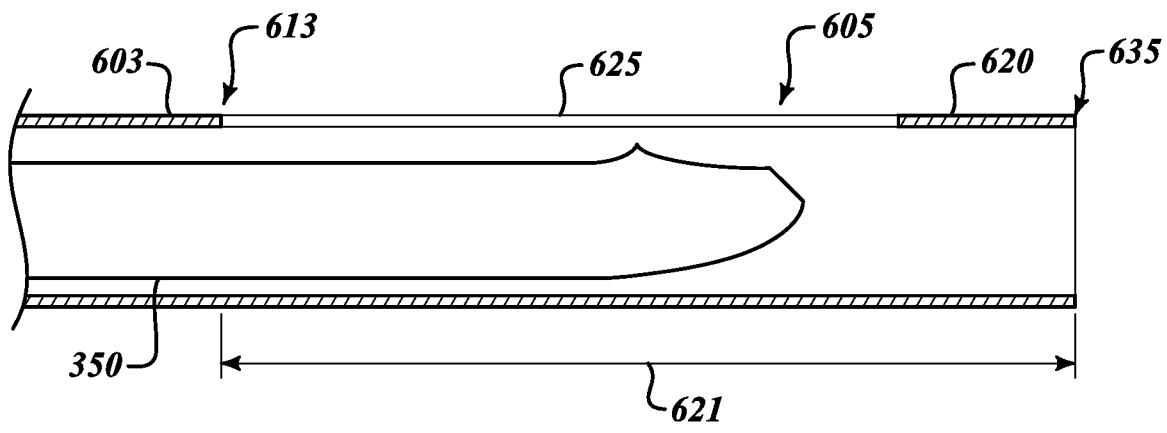
FIGS. 6 and 7 are cutaway views of an end of a sheath configured with another illustrative sheath tip having a distal member.
Figure 7:
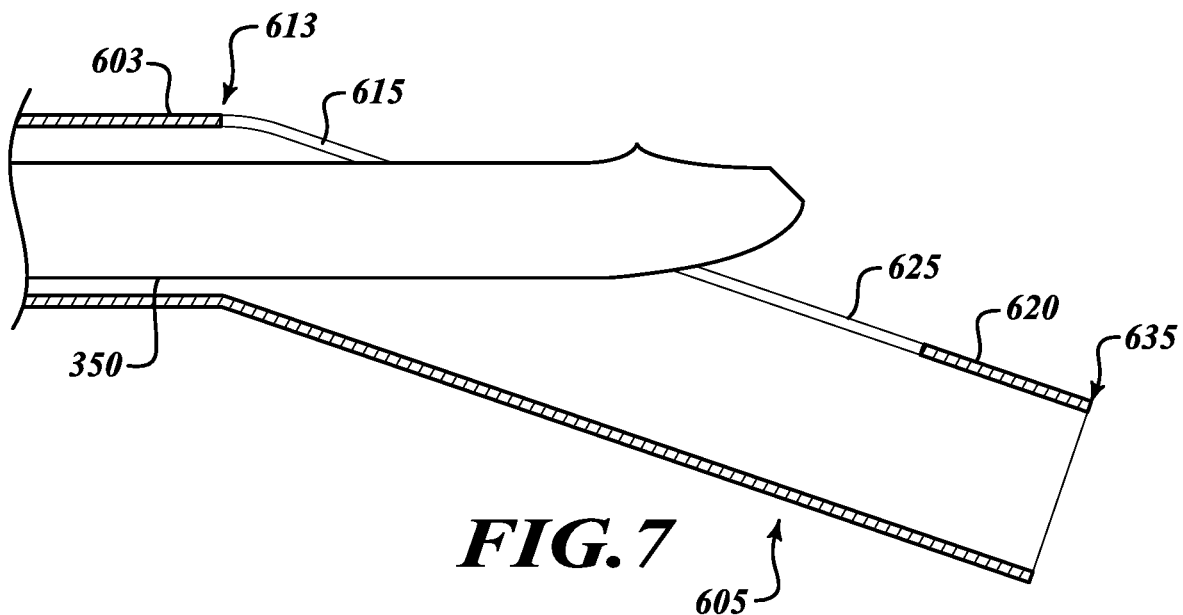

Referring to FIGS. 6 and 7, another illustrative embodiment of a sheath tip 605 incorporates a distal member 620. Referring to FIG. 6, a sheath 603 houses an elongated instrument 350, such as a sampling needle, similar to that as described with reference to FIG. 3. A sheath tip 605 includes a distal member 620 in the form of a section of the sheath tip 605 that defines an opening 625 through which the elongated instrument 350 may extend, as further described below. The sheath tip 605 may be integrally formed as part of the sheath 603 as the sheath 603 is molded, extruded, or otherwise formed. The sheath tip 605 also may be formed as a separate structure and then joined to the sheath 603, such as previously described with reference to FIG. 3. In either case, the opening 625 may be molded or cut into the sheath tip 605. Although not shown in FIG. 6, the sheath 603 and/or the sheath tip 605 may incorporate an insert as described with reference to FIG. 3, provided that the insert includes an opening that corresponds with the opening 625 in the sheath tip 605.

As explained below with reference to FIGS. 7 and 8, when an upper distal end 635 of the sheath tip 605 impacts a structure, such as a tissue surface, the sheath tip 605 may deflect while the elongated instrument 350 extends through the opening 625 instead of through the distal end 635 of the sheath tip 605. In an illustrative embodiment, the sheath tip 605 may be displaced from an end of the opening 625 that, therefore, constitutes a distal end 613 of the sheath 603. The distal member 620 thus extends a finite distance 621 from the distal end 613 of the sheath 603 at the end of the opening 625 through the end of the sheath tip 605.

Referring to FIG. 7, an impact (not shown in FIG. 7) on the upper distal end 635 of the sheath tip 605 may cause the sheath tip 605 to deflect away from the impact. As a result of the deflection of the sheath tip 605, the opening 625 may pass over at least a portion of the elongated instrument 350. The impact on the upper distal end 635 of the sheath tip 605 may result from impact with a tissue surface, as further described with reference to FIG. 8. With the deflection of the sheath tip 605, the distal member 620 is displaced from the elongated instrument 350 in a direction opposite the opening 625.

Figure 8:
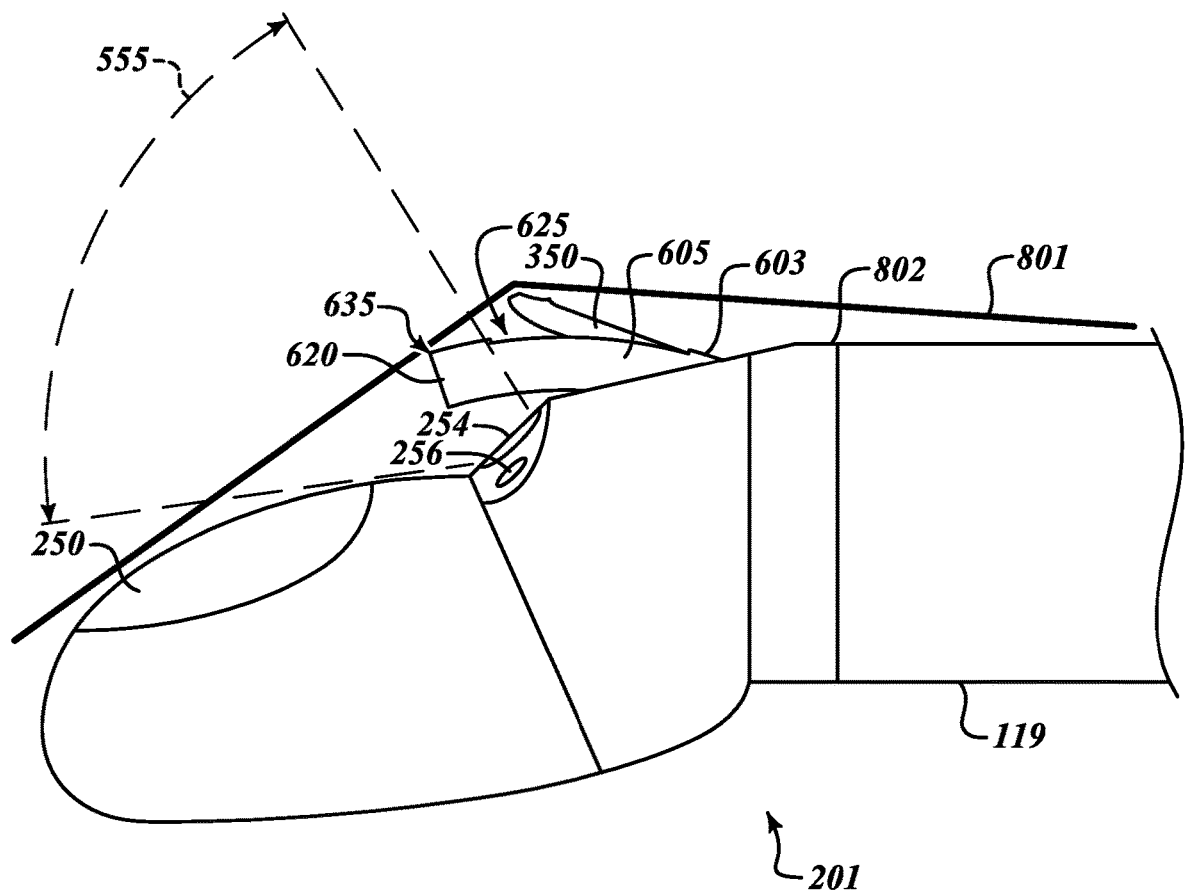
FIG. 8 is a side view of the head of the insertion device of FIG. 2 after extension of the sheath including a sheath tip having a distal member of FIGS. 6 and 7.

Referring to FIG. 8, the head 201 of the insertion device 119 is disposed adjacent a tissue surface 801. When the sheath 603 is extended from a first side 802 of the head 201 adjacent the tissue surface 801, the upper distal end 635 of the sheath tip 605 impacts upon the tissue surface 801, causing the distal member 620 to move away from the tissue surface 801 and into the detection range 555 of the camera 254 or another detection device, as was similarly described with reference to FIG. 5. The elongated instrument 350 is clear of the sheath 603 and able to operate, while presence of the distal member 620 in the detection range allows for verification of the position of the sheath 603, just as the distal member 220 allowed for the illustrative embodiments of FIGS. 2, 3, 4A, and 5.

Figure 9:
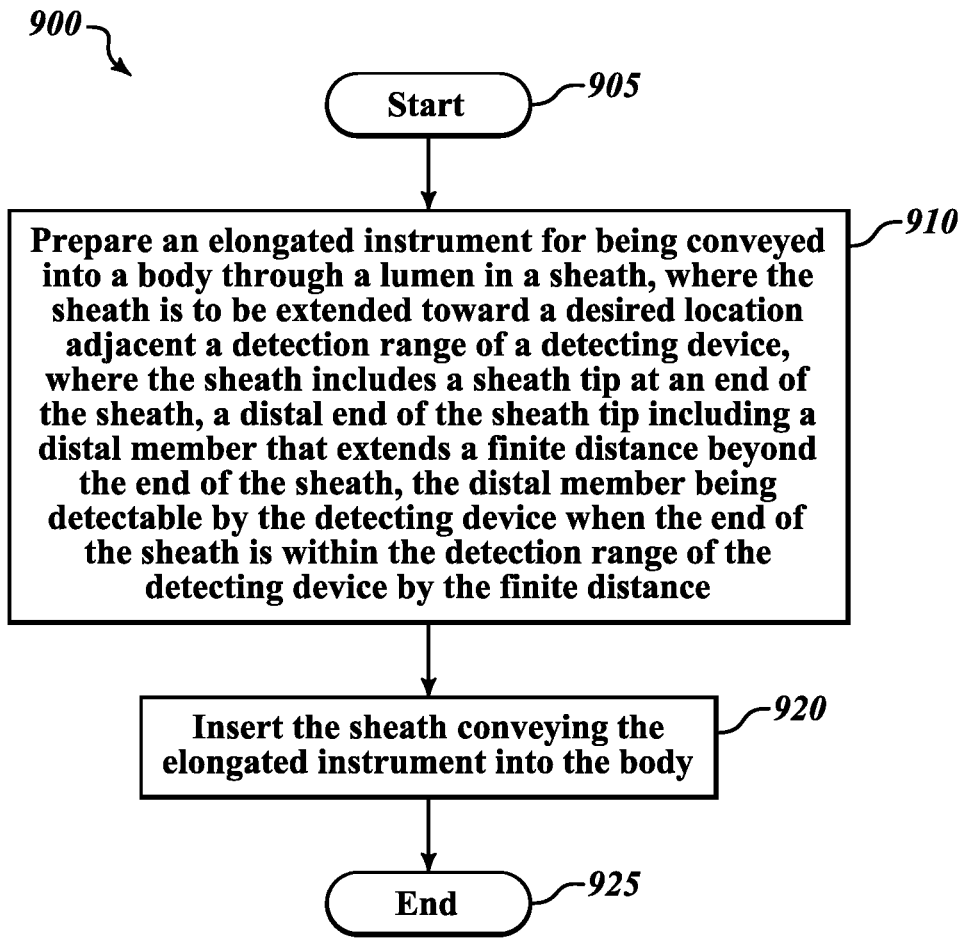
FIG. 9 is a flow diagram of an illustrative method of operating an apparatus equipped with a sheath tip having a distal member.

Referring to FIG. 9 an illustrative method 900 of using a sheath tip with a member as previously described. The method 900 starts at a block 905. At a block 910, an elongated instrument is prepared for being conveyed into a body through a lumen in a sheath, where the sheath is to be extended toward a desired location adjacent a detection range of a detecting device. The sheath includes a sheath tip at an end of the sheath, and a distal end of the sheath tip includes a distal member that extends a finite distance beyond the end of the sheath. The distal member is detectable by the detecting device when the end of the sheath is within the detection range of the detecting device by the finite distance. The configuration and operation of such sheath tips with distal members is described with reference to FIGS. 2, 3, 4A, 4B, 5, 6, 7, and 8.

At a block 920, the sheath conveying the elongated instrument is inserted into the body. The insertion of the elongated instrument is described with reference to FIGS. 1, 2, 5, and 8. The method 925 ends at a block 925.

It will be appreciated that the present descriptions of the sheath tips with distal members being used in the insertion of elongated instruments into a body via a sheath are not limiting to either the types of elongated instruments described or to use with medical instruments in a biological body. Sheath tips in the nature of those described could be used in any application where it may be desired to verify a position of a sheath when extending the sheath into a detection range of a detecting device could result in potentially harmful impingement of the sheath against the surface.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
  a sheath tip positionable at a distal end of a sheath configured to convey an elongated medical instrument that is movable independently of the sheath to a location adjacent a detection range of a detecting device, the sheath tip including an elongated distal member formed of a plastic and that is one of integrally formed with and fixedly attached to the sheath tip and that extends a fixed distance beyond a lip of the distal end that surrounds an opening through which the elongated medical instrument exits the distal end of the sheath, the elongated distal member being detectable by the detecting device with neither of the distal end of the sheath and the elongated medical instrument being extended within the detection range of the detecting device.

2. The apparatus of claim 1, wherein the sheath tip is an integral section of the sheath, the sheath tip being disposed at the distal end of the sheath.

3. The apparatus of claim 1, wherein the sheath tip is a separate structure configured to be attached to the distal end of the sheath.

4. The apparatus of claim 3, wherein the sheath tip is configured to be physically coupled to the distal end of the sheath at a sheath insert that is configured to be received within the lumen of the sheath.

5. The apparatus of claim 1, wherein the detecting device is one of at and adjacent to an end of an insertion device, the insertion device having a first side from which the sheath is configured to be extended along an axis toward a surface.

6. The apparatus of claim 5, wherein the elongated distal member is deformable and configured to be deflected by the surface away from the axis into the detection range of the detecting device.

7. The apparatus of claim 6, wherein the sheath defines a lumen configured to extend the elongated medical instrument toward the surface and the sheath tip is configured to extend the lumen to the distal end of the sheath tip.

8. The apparatus of claim 7, wherein the sheath tip defines an opening through which the elongated medical instrument extends along the axis toward the surface when the distal member is deflected by the surface.

9. The apparatus of claim 5, wherein the elongated distal member extends from a proximal side of the sheath tip adjacent the first side of the insertion device from which the sheath is configured to be extended.

10. The apparatus of claim 1, wherein the elongated distal member includes at least one longitudinal tongue extending the finite distance beyond the distal end of the sheath.

11. The apparatus of claim 1, wherein the tip is configured to be deformable.

12. The apparatus of claim 1, wherein the sheath tip has at least one characteristic chosen from a first thickness that is less than a second thickness of the sheath and a first rigidity that is less than a second rigidity of the sheath.

13. A system comprising:
a sheath defining therein a lumen and configured with a distal end extendable toward a surface;
an elongated medical instrument configured to be conveyed through the lumen in the sheath and that is movable independently of the sheath;
an insertion control system configured to convey the sheath along an axis to a desired location, wherein the insertion control system includes:
a detecting device disposed one of at and adjacent to an end of the insertion control system and having a detection range, and
a first side from which the sheath is configured to be extended along an axis toward a surface;
an instrument control system configured to direct operation of the elongated medical instrument when the elongated medical instrument reaches a desired position; and
a sheath tip positionable at the distal end of the sheath, the sheath tip including an elongated distal member formed of a plastic and that is one of integrally formed with and fixedly attached to the sheath tip and that extends a fixed distance beyond a lip of the distal end that surrounds an opening through which the elongated medical instrument exits the distal end of the sheath, the elongated distal member being detectable by a detecting device with neither of the distal end of the sheath and the elongated medical instrument being extended within the detection range of the detecting device.

14. The system of claim 13, wherein the sheath tip is one of:
an integral section of the sheath disposed at the distal end of the sheath; and
a separate structure configured to be attached to the distal end of the sheath.

15. The system of claim 13, wherein the elongated distal member is deformable and configured to be deflected by the surface away from the axis into the detection range of the detecting device.

16. The system of claim 13, wherein the sheath defines a lumen configured to extend the elongated medical instrument toward the surface and the sheath tip is configured to extend the lumen to the distal end of the sheath tip, and wherein the sheath tip defines an opening through which the elongated medical instrument extends along the axis toward the surface when the distal member is deflected by the surface.

17. The system of claim 13, wherein the elongated distal member extends from a proximal side of the sheath tip adjacent the first side of the insertion device from which the sheath is configured to be extended.

18. The system of claim 13, wherein the elongated distal member includes at least one longitudinal tongue extending the finite distance beyond the distal end of the sheath.

19. A method comprising:
preparing elongated medical instrument for being conveyed into a body through a lumen in a sheath, wherein the sheath is to be extended toward a desired location adjacent a detection range of a detecting device, wherein the sheath includes a sheath tip at a distal end of the sheath, the sheath tip including an elongated distal member formed of a plastic and that is one of integrally formed with and fixedly attached to the sheath tip and that extends a fixed distance beyond a lip of the distal end that surrounds an opening through which the elongated medical instrument exits the distal end of the sheath, the elongated distal member being detectable by the detecting device with neither of the distal end of the sheath and the elongated medical instrument being extended within the detection range of the detecting device; and
inserting the sheath conveying the elongated medical instrument into the body.

20. The method of claim 19, further comprising extending the sheath until the elongated distal member of the sheath tip is detected by the detecting device.

\* \* \* \* \*